US012508406B2

(12) United States Patent
Malek et al.

(10) Patent No.: US 12,508,406 B2
(45) Date of Patent: Dec. 30, 2025

(54) SYSTEMS AND METHODS FOR TREATING HYDROCEPHALUS

(71) Applicant: CEREVASC, INC., Auburndale, MA (US)

(72) Inventors: Adel M. Malek, Weston, MA (US); Carl Heilman, Wayland, MA (US)

(73) Assignee: CereVasc, Inc., Auburndale, MA (US)

( * ) Notice: Subject to any disclaimer, the term of this patent is extended or adjusted under 35 U.S.C. 154(b) by 266 days.

(21) Appl. No.: 18/483,509

(22) Filed: Oct. 9, 2023

(65) Prior Publication Data

US 2024/0115842 A1 Apr. 11, 2024

Related U.S. Application Data

(60) Provisional application No. 63/378,986, filed on Oct. 10, 2022.

(51) Int. Cl.
*A61M 25/00* (2006.01)
*A61M 27/00* (2006.01)

(52) U.S. Cl.
CPC ...... *A61M 27/006* (2013.01); *A61M 25/0075* (2013.01); *A61M 2210/1003* (2013.01)

(58) Field of Classification Search
CPC .. A61M 2025/0293; A61M 2210/1003; A61M 25/0075; A61M 27/006
See application file for complete search history.

(56) References Cited

U.S. PATENT DOCUMENTS

| | | | | |
|---|---|---|---|---|
| 6,110,139 A * | 8/2000 | Loubser | A61M 1/3623 604/4.01 |
| 11,497,552 B2 | 11/2022 | Morales | |
| 11,806,523 B2 | 11/2023 | Morales | |
| 2009/0125093 A1 | 5/2009 | Hansen | |
| 2012/0130468 A1 * | 5/2012 | Khosravi | A61M 25/104 623/1.11 |
| 2020/0030588 A1 | 1/2020 | Heilman et al. | |
| 2020/0368506 A1 | 11/2020 | Malek et al. | |
| 2020/0376239 A1 | 12/2020 | Heilman et al. | |
| 2021/0268252 A1 | 9/2021 | Malek et al. | |

FOREIGN PATENT DOCUMENTS

| | | |
|---|---|---|
| EP | 1839602 B1 | 7/2009 |
| WO | WO 2009/036039 A1 | 3/2009 |
| WO | WO 2016/070147 A1 | 5/2016 |
| WO | WO 2022006317 | 1/2022 |
| WO | WO 2023212161 A1 | 11/2023 |

OTHER PUBLICATIONS

Extended European Search Report for EP Patent Appln. No. 23197404.9 dated Jan. 16, 2024.

* cited by examiner

*Primary Examiner* — Kai H Weng
(74) *Attorney, Agent, or Firm* — Vista IP Law Group, LLP

(57) ABSTRACT

Methods for deploying and removing an endovascular cerebrospinal fluid (CSF) shunt device in a patient's spinal subarachnoid space or third ventricle are disclosed herein. The disclosed methods can be used to treat elevated CSF pressure (e.g., acquired communicating hydrocephalus, pseudotumor cerebri), normal pressure hydrocephalus, or as a temporary measure to drain CSF and/or blood from the subarachnoid space instead of inserting an external ventricular drain in the patient.

11 Claims, 10 Drawing Sheets

SYSTEMS AND METHODS FOR TREATING HYDROCEPHALUS

CROSS REFERENCE TO RELATED APPLICATION

This application claims the benefit of U.S. Provisional Patent Application Ser. No. 63/378,986, filed on Oct. 10, 2022, the entire disclosure of which is expressly incorporated by reference herein.

FIELD OF THE INVENTION

The inventions disclosed herein relate to systems and methods for accessing subarachnoid spaces and draining cerebrospinal fluid (CSF), (e.g., to relieve elevated intracranial pressure or treat normal pressure hydrocephalus), using an endovascular approach. More particularly, the present disclosure pertains to systems and methods for treatment of hydrocephalus, pseudotumor cerebri, and/or intracranial hypertension.

BACKGROUND

Hydrocephalus is one of the most common and important neurosurgical conditions affecting both, children and adults. Hydrocephalus, meaning "water on the brain," refers to the abnormal CSF accumulation in the brain. The excessive intracranial pressure resulting from hydrocephalus can lead to a number of significant symptoms ranging from headache to neurological dysfunction, coma, and death.

Cerebrospinal fluid is a clear, physiologic fluid that bathes the entire nervous system, including the brain and spinal cord. Cells of the choroid plexus present inside the brain ventricles produce CSF. In normal patients, cells within arachnoid granulations reabsorb CSF produced in the choroid plexus. Arachnoid granulations straddle the surface of the intracranial venous drainage system of the brain and reabsorb CSF present in the subarachnoid space into the venous system. Approximately 450 mL to 500 mL of CSF is produced and reabsorbed each day, enabling a steady state volume and pressure in the intracranial compartment of approximately 8-16 cm $H_2O$. This reabsorption pathway has been dubbed the "third circulation," because of its importance to the homeostasis of the central nervous system.

Hydrocephalus occurs most commonly from the impaired reabsorption of CSF, and in rare cases, from its overproduction. The condition of impaired reabsorption is referred to as communicating hydrocephalus. Hydrocephalus can also occur as a result of partial or complete occlusion of one of the CSF pathways, such as the cerebral aqueduct of Sylvius, which leads to a condition called obstructive hydrocephalus.

A positive pressure gradient between the CSF pressure of the subarachnoid space and the blood pressure of the venous system may contribute to the natural absorption of CSF through arachnoid granulations. For example in non-hydrocephalic individuals, CSF pressures can range from about 6 cm H20 to about 20 cm H20. ICSF pressure greater than 20 cm H20 is considered pathological of hydrocephalus, although the CSF pressure in some forms of the disease can be lower than 20 cm H20. Venous blood pressure can range from about 4 cm H20 to about 11 cm H20 in non-hydrocephalic patients, and can be slightly elevated in diseased patients. While posture changes in patients, e.g., from supine to upright, affect CSF and venous pressures, the positive pressure gradient between the SAS and venous pressure remains relatively constant. Momentary increases in venous pressure greater than CSF pressure, however, can temporarily disturb this gradient, for example, during episodes of coughing, straining, or valsalva.

Normal pressure hydrocephalus (NPH) is one form of communicating hydrocephalus. NPH patients typically exhibit one or more symptoms of gait disturbance, dementia, and urinary incontinence, which can lead to misdiagnosis of the disease. Unlike other forms of communicating hydrocephalus, NPH patients may exhibit little or no increase in CSF pressure. It is believed that the CSF-filled ventricles in the brain enlarge in NPH patients to accommodate the increased volume of CSF in the subarachnoid space. For example, while non-hydrocephalic patients typically have CSF pressures ranging from about 6 cm H20 to about 20 cm H20, CSF pressure in NPH patients can range from about 6 cm H20 to about 27 cm H20. It has been suggested that NPH is typically associated with normal CSF pressures during the day and intermittently increased CSF pressure at night.

Other conditions characterized by elevated CSF pressure include pseudotumor cerebri (e.g., benign intracranial hypertension). The elevated CSF pressure of pseudotumor cerebri causes symptoms similar to, but that are not, a brain tumor. Such symptoms can include headache, tinnitus, dizziness, blurred vision or vision loss, and nausea. While most common in obese women 20 to 40 years old, pseudotumor cerebri can affect patients in all age groups.

Prior art techniques for treating communicating hydrocephalus (and in some cases, pseudotumor cerebri and intracranial hypertension) rely on ventriculoperitoneal shunts ("VPS" or "VP shunt" placement), a medical device design introduced more than 60 years ago. VPS placement involves an invasive surgical procedure performed under general anesthesia, typically resulting in hospitalization ranging from two to four days. The surgical procedure typically involves placement of a silicone catheter in the frontal horn of the lateral ventricle of the brain through a burr hole in the skull. The distal portion of the catheter leading from the lateral ventricle is then connected to a pressure or flow-regulated valve, which is placed under the scalp. A separate incision is then made through the abdomen, into the peritoneal cavity, into which the proximal portion of a tubing catheter is placed. The catheter/valve assembly is then connected to the tubing catheter, which is tunneled subcutaneously from the neck to the abdomen.

VPS placement is a very common neurosurgical procedure, with estimates of 55,000-60,000 VPS placements occurring in the U.S. each year. While the placement of a VP shunt is typically well-tolerated by patients and technically straightforward for surgeons, VP shunts are subject to a high rate of failure in treated patients. Complications from VP shunt placement are common with a one-year failure rate of approximately 40% and a two-year shunt failure rate reported as high as 50%. Common complications include catheter obstruction, infection, over-drainage of CSF, and intra-ventricular hemorrhage. Among these complications, infection is one of the most serious, since infection rates in adults are reported between 1.6% and 16.7%. These VPS failures require "shunt revision" surgeries to repair/replace a portion or the entirety of the VP shunt system, with each of these revision surgeries carrying the same risk of general anesthesia, post-operative infection, and associated cost of hospitalization as the initial VPS placement; provided, however that shunt infections can cost significantly more to treat (e.g., three to five times more) compared to initial VP shunt placement. Often these infections require additional hospital stays where the proximal portion of the VPS is externalized and long-term antibiotic therapy is instituted. The rate of failure is a constant consideration by clinicians as they assess patients who may be candidates for VPS placement. Age, existing co-morbidities and other patient-specific factors are weighed against the likelihood of VP shunt failure that is virtually assured during the first 4-5 years following initial VP shunt placement.

External ventricular (EVD) drains comprise the ventricular catheter portion of the VP shunt, but are used to drain CSF from the intracranial SAS to a bag or other collection vessel at the bedside. EVDs are typically utilized on an acute basis, for example, in patients following a subarachnoid hemorrhage, to drain CSF and blood from the SAS. EVD's are placed through a burr hole drilled in the skull with the EVD catheter tunneled through the brain into the lateral ventricle. Like the ventricular catheter of VP shunt devices, EVDs are prone to clogging from choroid plexus or blood cells in the CSF. In addition, EVDs are prone to infection with reported mean infection rate of 9% with higher infection rates observed in certain patient cohorts.

Despite significant advances in biomedical technology, instrumentation, and medical devices, there has been little change in the design of basic VPS hardware or EVDs since their introduction in neurosurgery several decades ago.

SUMMARY

In accordance with embodiments of the inventions, a method for draining cerebrospinal fluid (CSF) from a patient's lumbar subarachnoid space (LSAS) to a venous system is disclosed. The method comprises advancing a delivery catheter from a venous access location in the patient and through an inferior vena cava in a caudal direction, the delivery catheter comprises a lumen with an opening on a distal portion of the catheter and an endovascular CSF shunt disposed within the lumen; further advancing the deliver catheter through an azygos vein to a venous branch adjacent or proximate a nerve root, the nerve root extending through a spinal foramen into the LSAS; penetrating through a venous endothelial layer of the venous branch and a dura layer surrounding the nerve root to access the LSAS via the venous branch and azygous vein; deploying a distal portion of the shunt in the LSAS and a proximal portion of the shunt in the venous branch or azygos vein such that a body of the shunt extends through the dura layer, the shunt comprises at least one CSF inlet in the distal portion, a fluid lumen, and a CSF outlet in the proximal portion, the shunt CSF inlet, lumen, and CSF outlet in fluid communication; and draining CSF from the LSAS through the CSF inlet, lumen, and CSF outlet of the shunt into the venous branch or azygos vein.

In some embodiments, the delivery catheter further comprises a penetrating element disposed on or coupled to the distal portion of the catheter, wherein penetrating the endothelial layer and dura layer to access the LSAS from the venous branch and azygous vein comprises advancing the delivery catheter and penetrating element through the endothelium and dura such that the open of the delivery catheter is disposed within the spinal SAS.

In further embodiments, the shunt further comprises a penetrating element disposed on or coupled to the distal portion of the shunt, wherein penetrating the endothelial and dura layers to access the LSAS from the venous branch and azygous vein comprises advancing the shunt and penetrating element through the dura, such that the CSF inlet of the shunt is disposed within the LSAS.

Optionally, the shunt comprises an expandable anchor disposed on or coupled to the distal portion of the shunt and wherein deploying the distal portion of the shunt in the LSAS further comprises expanding the anchor to secure the distal shunt portion in the LSAS. Optionally, expanding the anchor further comprises recessing the penetrating element inside an outer perimeter of the expanded anchor.

In some embodiments, the delivery catheter further comprises a stent disposed around the distal portion of the catheter, the method further comprises expanding the stent in the venous branch or azygos vein to secure the distal portion of the catheter in the vessel.

In some embodiments, penetrating the endothelial and dura layers to access the LSAS from the venous branch and azygous vein comprises advancing a needle disposed within the delivery catheter lumen from the opening in the distal catheter portion and further advancing the needle through the dura layer into the LSAS. The needle comprises a needle lumen and an opening in a distal portion of the needle lumen, the shunt disposed within the needle lumen, wherein deploying the distal portion of the shunt in the LSAS comprises advancing the shunt distally through the needle lumen and needle opening into the LSAS.

Optionally, the disclosed method further comprises acquiring imaging data and generating a 3D reconstruction of an intended pathway from the venous branch or azygos vein through the dura layer to the LSAS, and using the 3D reconstruction to facilitate navigation of the delivery catheter or shunt from the venous branch into the LSAS. The imaging data may comprise ultrasound or optical coherence tomography.

In accordance with embodiments of the inventions, a method for draining cerebrospinal fluid (CSF) from a patient's subarachnoid space (SAS) to a venous system is disclosed. The method comprises advancing a delivery catheter from a venous access location in the patient through a straight sinus, the delivery catheter comprises a lumen with an opening on a distal portion of the catheter and an endovascular CSF shunt disposed within the lumen; further advancing the deliver catheter into an internal cerebral vein; penetrating a venous endothelial layer of the internal cerebral vein to access a third ventricle; deploying a distal portion of the shunt in the third ventricle and a proximal portion of the shunt in the internal cerebral vein such that a body of the shunt extends through the venous endothelial layer, the shunt comprises a CSF inlet in the distal portion, a fluid lumen, and a CSF outlet in the proximal portion, the shunt CSF inlet, lumen, and CSF outlet in fluid communication; and draining CSF from the third ventricle through the CSF inlet, lumen, and CSF outlet of the shunt into the internal cerebral vein.

In some embodiments, the delivery catheter further comprises a penetrating element disposed on or coupled to the distal portion of the catheter, wherein penetrating the venous endothelial layer comprises advancing the delivery catheter and penetrating element through venous endothelium, such that the opening of the delivery catheter lumen is disposed within the third ventricle.

In some embodiments, the shunt further comprises a penetrating element disposed on or coupled to the distal portion of the shunt, wherein penetrating the venous endothelial layer to access the third ventricle from the internal cerebral vein comprises advancing the shunt and penetrating element through venous endothelium, such that the penetrating element and CSF inlet of the shunt are disposed within the third ventricle.

In some embodiments, the shunt comprises an expandable anchor disposed on or coupled to the distal portion of the shunt and wherein deploying the distal portion of the shunt in the third ventricle further comprises expanding the anchor to secure the distal shunt portion in the ventricle. Optionally, expanding the anchor further comprises recessing the penetrating element inside an outer perimeter of the anchor.

Optionally, the delivery catheter further comprises a stent disposed around the distal portion of the catheter, the method further comprises expanding the stent in the internal cerebral vein to secure the distal portion of the catheter in the vein.

Optionally, penetrating the venous endothelial layer to access the third ventricle from the internal cerebral vein comprises advancing a needle from the opening of the delivery catheter lumen and further advancing the needle through the venous endothelium into the third ventricle. The needle comprises a needle lumen and an opening in a distal portion of the lumen, the shunt disposed within the needle lumen, wherein deploying the distal portion of the shunt in the third ventricle comprises advancing the shunt distally through the needle lumen and opening into the ventricle.

Optionally, the disclosed method comprises acquiring imaging data and generating a 3D reconstruction of an intended pathway from the internal cerebral vein through the venous endothelium into the third ventricle, and using the 3D reconstruction to facilitate navigation of the delivery catheter or shunt from the internal cerebral vein into the third ventricle.

In some embodiments, the disclosed method further comprises navigating an endovascular retrieval device through a patient's vasculature until the retrieval device is located at or proximate to the proximal portion of the shunt; grasping or capturing the proximal portion of the shunt with the retrieval device; and removing the shunt from the LSAS and the patient with the retrieval device.

Other and further aspects and features of embodiments will become apparent from the ensuing detailed description in view of the accompanying figures.

DETAILED DESCRIPTION OF THE ILLUSTRATED EMBODIMENTS

Figure 1A:
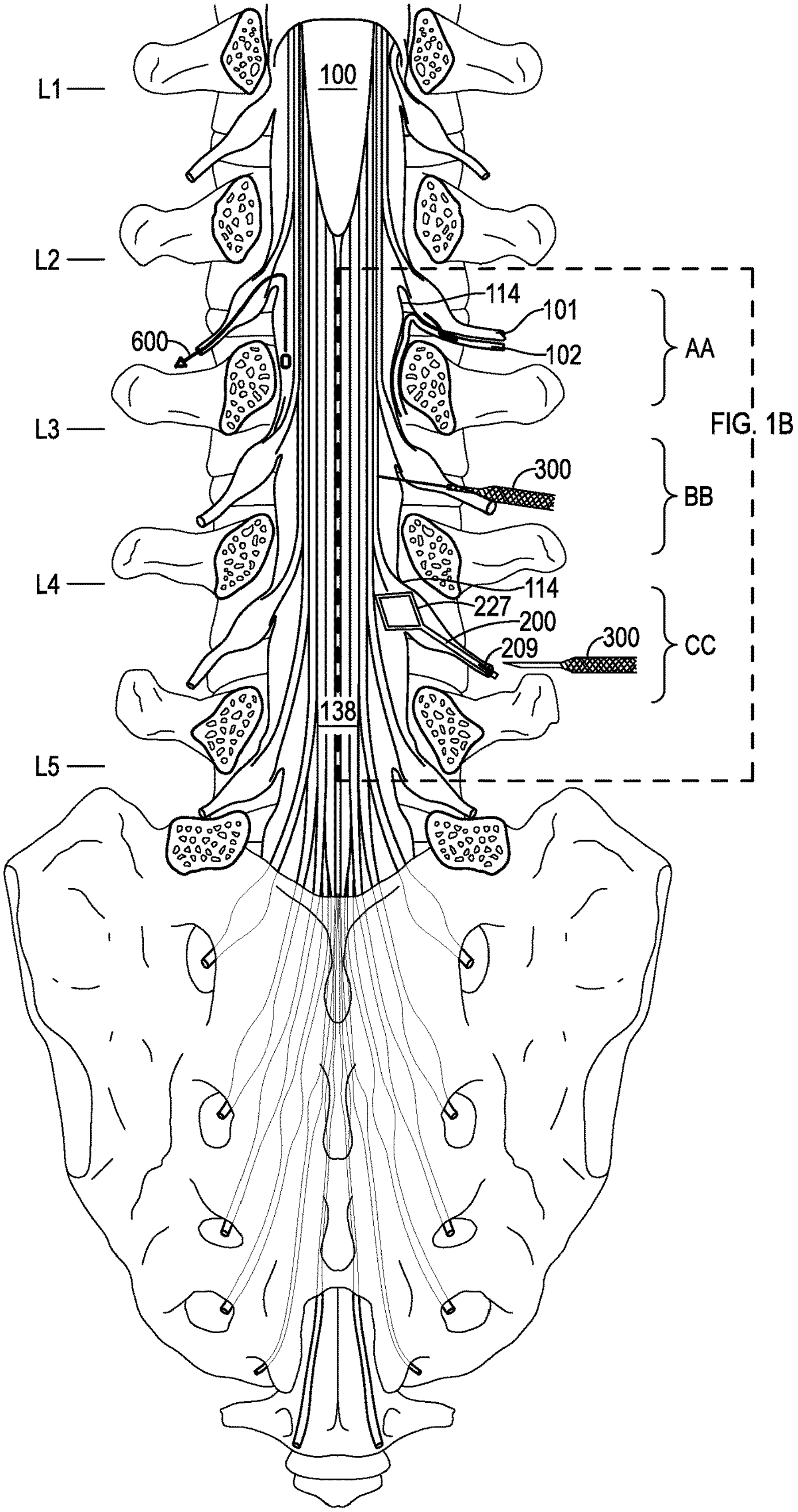
FIGS. 1A-1B are a schematic diagram of a lumbar subarachonoid space of a human patient and depicts endovascular CSF shunt devices according to embodiments of the disclosed inventions.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skilled in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments are described hereinafter with reference to the figures. The figures are not necessarily drawn to scale, the relative scale of select elements may have been exaggerated for clarity, and elements of similar structures or functions are represented by like reference numerals throughout the figures. It should also be understood that the figures are only intended to facilitate the description of the embodiments, and are not intended as an exhaustive description of the invention or as a limitation on the scope of the invention, which is defined only by the appended claims and their equivalents. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

Disclosed and depicted herein are systems, devices and methods for use in performing minimally invasive surgical procedures in extravascular spaces including the subarachnoid space (SAS). The disclosed devices can be used in the venous vasculature to pass through a vessel wall and/or other tissue to access a location outside the vasculature. Non-limiting examples include transvenous neurosurgery. In the context of minimally invasive neurosurgical procedures, the disclosed systems and devices advantageously avoid the need for drilling a hole in the patient's skull in order to access areas surrounding the brain and/or spinal cord, as well as brain tissue during a surgical procedure. In addition, disclosed and depicted herein are methods and devices for deploying an endovascular CSF shunt device to drain CSF from the subarachnoid space to another location in the body. In comparison to conventional CSF shunt devices or other endovascular CSF shunt devices, the disclosed methods and devices can be deployed to minimize the risk of CSF over drainage as further described below. While the following detailed description relates to transvenous neurosurgical procedures, the disclosure is provided for purposes of explanation and illustration only, and it should be appreciated that the disclosed systems and devices can be used elsewhere in the vasculature to access an extravascular location by passing through a blood vessel wall.

Figure 3:
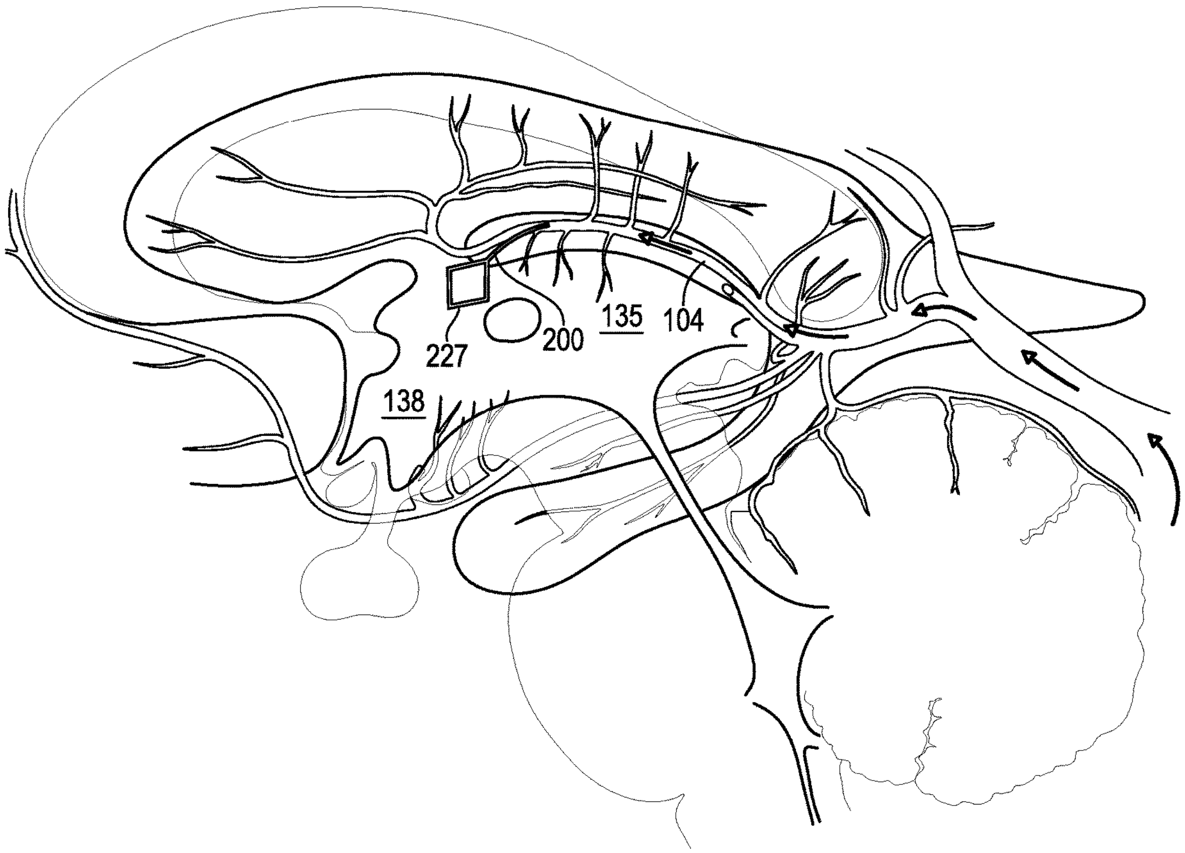
FIG. 3 is a sagittal view of the human brain and depicts an endovascular CSF shunt device according to embodiments of the disclosed inventions.
Figure 4A:
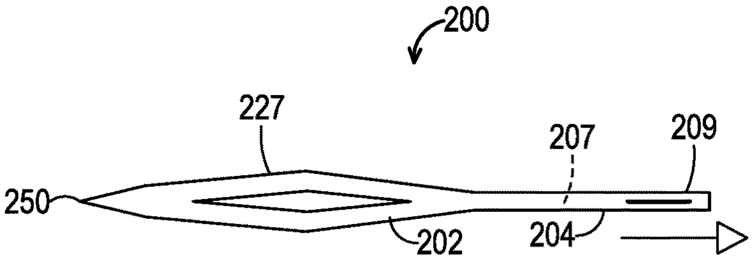
FIGS. 4A-C depict an endovascular CSF shunt device according to embodiments of the disclosed inventions.
Figure 4B:
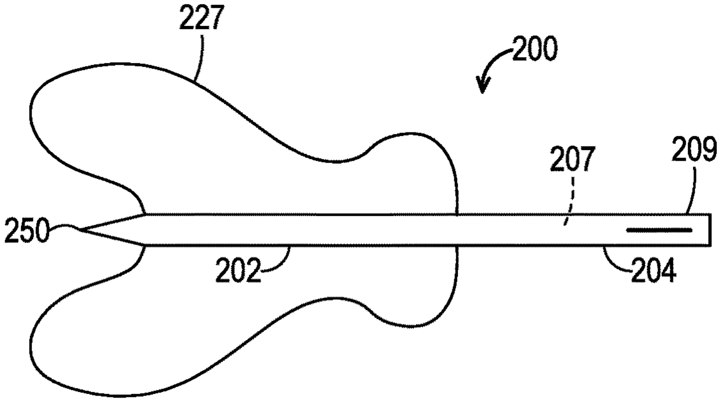

A delivery catheter 300 can be used to deploy embodiments of an endovascular shunt 200. The delivery catheter 300 can include a lumen 305 extending from an opening in a proximal portion of the catheter (e.g., in a handle, not shown) to an opening 346 in a distal portion 344 of the catheter 300. In some embodiments of the delivery catheter 300, the distal portion 344 of the catheter comprises a penetrating element 350 in fluid communication with the opening 346 and the lumen 305 of the distal portion 344 of the delivery catheter 300. The delivery catheter 300 can include a retractable guard member (not shown) disposed over penetrating element 350, such that the penetrating element 350 is covered during navigation of the delivery catheter 300 towards a target deployment site of a shunt 200. Additionally, the penetrating element 350 can be exposed by retracting the guard member prior to accessing the SAS with the delivery catheter 300. The shunt 200 is loaded into and navigated through the lumen 305 of the delivery catheter 300 and deployed out the opening 346 in the distal portion 344 of the catheter having the penetrating element 350 (portion CC of FIGS. 1A-16). In other embodiments, the delivery catheter 300 does not include the penetrating element at the distal portion 344 of the catheter; instead, a needle 352 can be advanced through the delivery catheter lumen 305 out of the opening 346 of the catheter to access the SAS (portion BB of FIGS. 1A-1B) and the shunt 200 can be deployed through the needle (not shown). The shunt 200 comprises a proximal portion 204 and a distal portion 202. Alternatively, the shunt 200 can include a penetrating element 250 coupled to or disposed on the distal portion 202 of the shunt 200 (FIGS. 4A-4B). The shunt 200 is configured to be translated through the lumen 305 of delivery catheter 300 using a pusher (not shown). Embodiments of the delivery catheter 300 and the shunt 200 that can be used to perform the methods disclosed herein are described in U.S. patent application Ser. No. 16/998,606 (Pub. No. 2020/0376239), U.S. patent application Ser. No. 16/986,245 (Pub. No. 2020/0368506), U.S. patent application Ser. No. 16/337,346 (Pub. No. 2020/0030588), and U.S. patent application Ser. No. 17/317,027 (Pub. No. 2021/0268252). The contents of the foregoing applications are hereby incorporated by reference into the present application in their entirety.

Figure 1B:
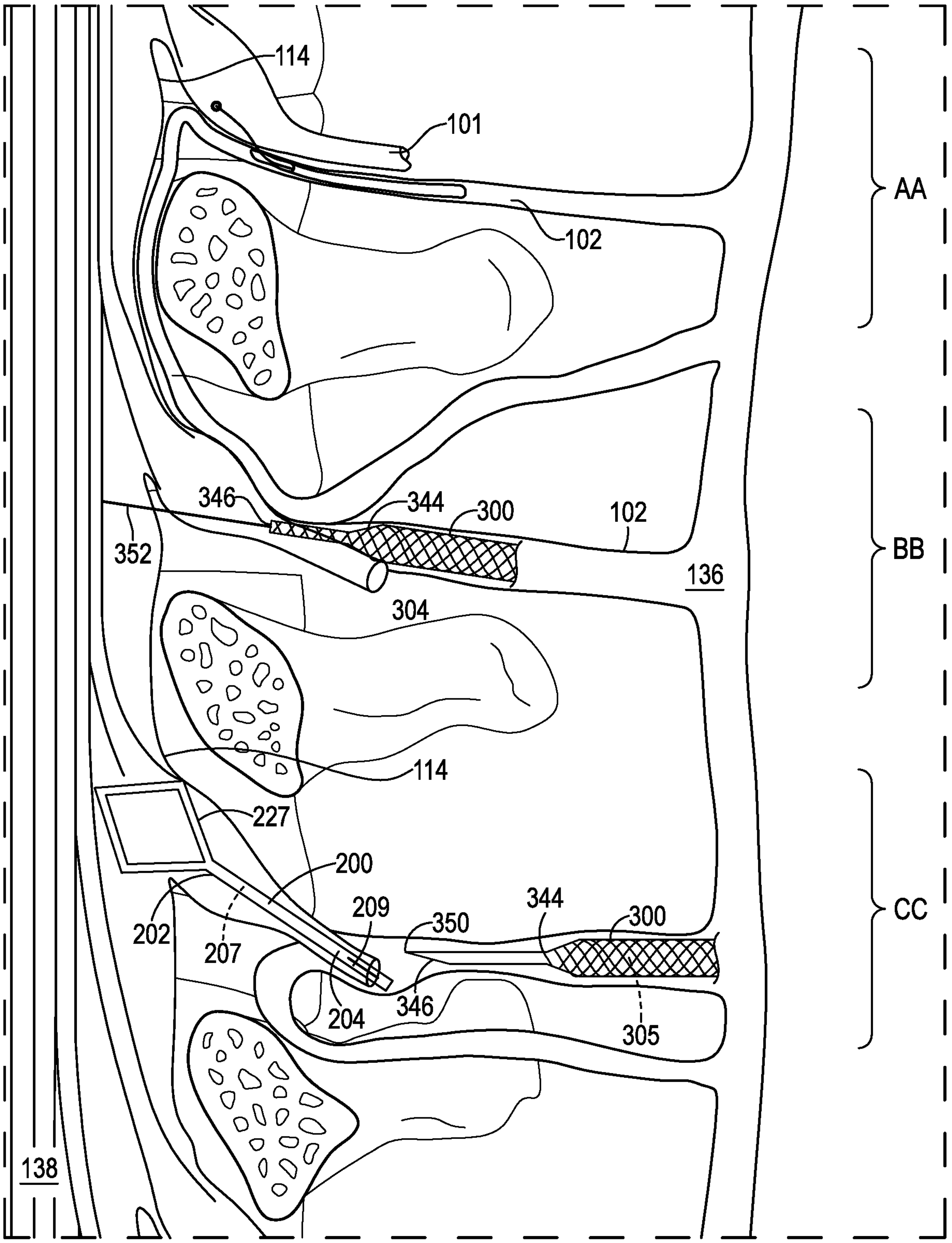
Figure 2:
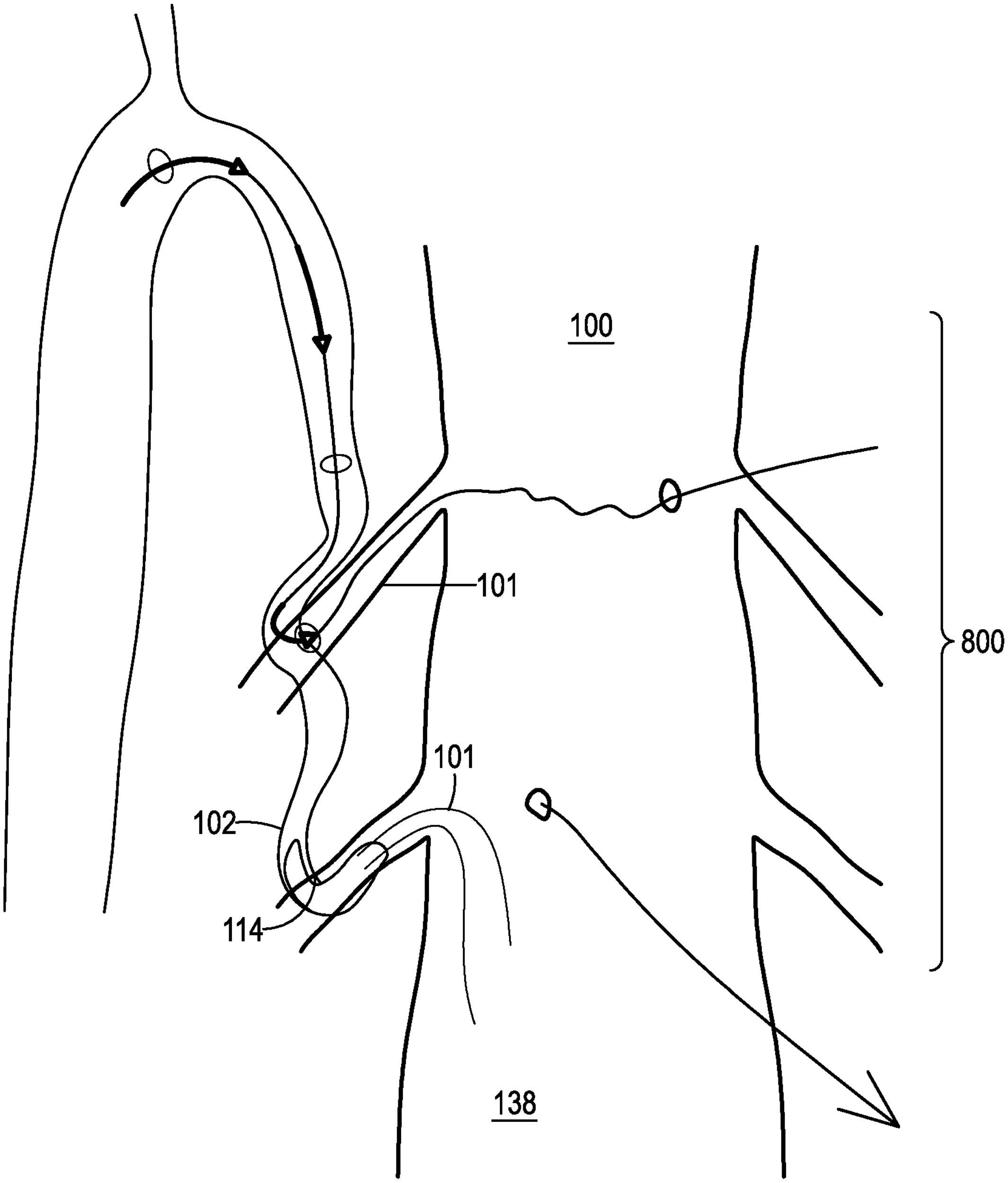
FIG. 2 is a schematic diagram of a thoracic subarachonoid space of a human patient including depictions of an endovascular CSF shunt device according to embodiments of the disclosed inventions.

FIG. 1A is a schematic diagram depicting a caudal portion of the spinal cord 100 and a CSF-filled lumbar subarachonoid space ("LSAS") 138 of a human patient. FIG. 1B is a detailed section of FIG. 1A to better appreciate the embodiments depicted in portions labelled as AA-CC. For reference, the axial level of the lumbar vertebrae L1 through L5 are depicted in FIG. 1A. The LSAS 138 is contained beneath a dura layer 114 (i.e., dura layer or thecal sac), as shown in FIG. 1A, and the interior wall (i.e., CSF contacting portion) of the dura layer 114 is lined with an arachnoid layer 115 (not shown). As shown in FIGS. 1A-1B, the venous branches 102 surround, extend adjacent to or alongside the dura layer 114 surrounding the nerve root 101. The nerve root 101 passes through a foramen in the spine, into the LSAS, and is connected to the spinal cord 100. The dura layer 114 surrounds nerve root 101 and the venous branches 102 surrounds or extends adjacent to the dura layer 114 surrounding the nerve root 101. The venous branches 102 further extend away from the LSAS 138 to a connection with the azygos vein 136 (FIG. 1B) and the azygos veins 136 extend to a connection with the caudal vena cava (FIG. 2).

Embodiments of the disclosed inventions can be used to treat hydrocephalus and/or elevated intracranial pressure (e.g., idiopathic intracranial hypertension) by advancing the delivery catheter 300 through the superior or inferior vena cava and further through any vein that connects with a venous branch surrounding or extending adjacent to or proximate a never root. Then, the delivery catheter 300 would be extending through dura layer 114 surrounding the nerve root 101 further through a foramen in the spine and entering the CSF-filled subarachnoid space. These venous branches surround or lie adjacent to or contiguous with the dura layer 114 surrounding nerve roots 101 such that the delivery catheter 300 and the shunt 200 can pass through venous endothelium and dura layer 114 to access the CSF-filled subarachnoid space, and drain CSF from the subarachnoid space through the shunt 200 and into the venous system. Embodiments of the disclosed inventions advantageously provide the interventionalist with an opportunity to select the shunt 200 deployment location during the endovascular procedure due to the extensive venous network communicating with veins that branch adjacent foramen and dura layer 114 surrounding the nerve root 101, as the nerve root enters the spinal subarachnoid space using the imaging methods, without the need for extensive pre-procedure anatomical screening and identification of a target shunt deployment location.

A variety of different imaging methods can be used to ensure accurate positioning of the shunt 200 and delivery catheter 300. Examples of suitable imaging methods include biplane fluoroscopy, digital subtraction angiography with road mapping technology, venous angiography with road mapping technology, 3D-rotational angiography or venography (3DRA or 3DRV), and cone-beam computed tomographic angiography or venography (CBCTA or CBCTV). Optionally, these imaging methods can be combined, fused, or overlaid with CT or MR imaging to provide additional guidance to the clinician. Both 3DRA/V and CBCTA/V enable volumetric reconstruction showing the relationship between the bony anatomy of the spine, the venous anatomy and the radiopaque markers on the delivery catheter and shunt used for shunt deployment. The methods of deploying the shunt 200 comprise imaging the shunt 200 while deploying the shunt 200 in the patient.

Further, if the shunt 200 is no longer needed by the patient or if the shunt 200 over-drains CSF, a clinician can stop CSF flow through the shunt 200 by embolizing (e.g., using a liquid embolic material or embolic coils) the venous branch lumen where the shunt 200 is draining CSF into the venous system. Thus, sacrificing the venous branch 102 in this manner present little, if any, risk to the patient due to the extensive venous network surrounding or adjacent to the spinal column. Alternatively, the shunt 200 may be removed from the patient by suitable techniques, where an exemplary path out of the patient's body is shown by arrow 600 in FIG. 1A.

Referring back to FIGS. 1A-1B, the endovascular CSF shunts 200 can be deployed via the venous branch 102, such that a CSF inlet portion of the shunt 200 is disposed within the CSF-filled LSAS 138. In portion CC of FIGS. 1A-1B, the shunt 200 comprises an anchoring mechanism 227 (i.e., distal anchor or anchoring mechanism) on the distal portion 202 of the shunt; when the shunt 200 is deployed, the anchoring mechanism 227 expands and is disposed within the LSAS 138, and the proximal portion 204 of the shunt 200 is disposed in the venous branch 102. Embodiments of the shunt 200 include a CSF lumen 207 extending between the distal portion 202 and the proximal portion 204 of the shunt, with one or more CSF inlet openings in the distal portion 202 and one or more CSF outlet openings in the proximal portion 204. The CSF inlet opening(s) and CSF outlet opening(s) are in fluid communication with CSF lumen 207 such that, when the distal portion 202 of the shunt 200 is deployed within a CSF-filled LSAS 138, CSF will flow from the LSAS through the one or more CSF intake openings, through CSF lumen 207, and out of the CSF outflow openings in the proximal portion 204 of the shunt 200. One or more one-way valve 209 or any other flow regulating mechanisms can be disposed in or coupled to a portion (e.g., proximal 204, body 203 and/or distal 202 portions) of the shunt 200 to regulate the CSF flow rate through the shunt 200 and prevent backflow of blood or other body fluid through the CSF lumen 207 into the LSAS 138. Thus, with reference to portion CC of FIGS. 1A-1B, the shunt 200 drains CSF from the LSAS 138 through CSF lumen 207 and out of valve 209 into venous branch 102.

Embodiments of the shunt 200 capitalize on a favorable pressure gradient between the subarachnoid space and venous system or other drainage location to drive CSF through the shunt 200 (i.e., inner lumen 207). In patients without hydrocephalus or elevated intracranial pressure, the normal differential pressure between the CSF of the subarachnoid space and blood pressure of the venous system is about 5 to 12 cm $H_2O$; this differential pressure between the subarachnoid space and venous system can be significantly higher in hydrocephalic patients or in patients with elevated intracranial pressure. Once deployed and implanted, the shunt 200 facilitates one-way flow of CSF from the subarachnoid space into the venous system where CSF is carried away by venous circulation, similar to the way that normally functioning arachnoid granulations drain CSF into the venous system. The shunt 200 prevents backflow of venous blood into subarachnoid space via one or more one-way valves 209 or any other flow regulating mechanisms. The shunt 200 allows for a more physiologic drainage of CSF by directing CSF directly into the venous system, a process that occurs naturally in people without hydrocephalus. In this manner, the pressure created by the excess CSF in the subarachnoid space is relieved, and patient symptoms due to hydrocephalus can thereby be ameliorated or even eliminated. In some embodiments, the shunt 200 can include a one-way valve 209 at the proximal portion 204 of the shunt 200 (FIGS. 1A-1B) as the flow regulating mechanism configured to regulate fluid flow through the shunt 200 into the venous system.

In embodiments of the inventions, a target flow rate of CSF (e.g., in a range of about 5 ml per hour to about 15 ml per hour) through the shunt 200 at a normal differential pressure is defined as being in a range between about 5 cm $H_2O$ to about 12 cm $H_2O$ between the subarachnoid space and venous system.

In some embodiments, a target flow rate of CSF through the shunt 200 and/or valve 209 is approximately 10 ml per hour at a range of differential pressure between the subarachnoid space and venous system ("ΔP") between 0.5 to 8 mmHg. A maximum flow rate of CSF through the shunt 200 and/or valve 209 can exceed 20 ml per hour and typically occurs immediately after shunt implantation in a patient with elevated CSF pressure (e.g., CSF pressure greater than 20 cm $H_2O$). The valve 209, as the flow regulating mechanism of the shunt 200, comprises a normal operating range (CSF flow direction) of 0.5 to 8 mmHg or higher ΔP, and a reverse opening pressure (backflow prevention) of at least −40 mmHg ΔP.

A positive pressure gradient between the CSF pressure of the subarachnoid space and the blood pressure of the venous system contributes to the natural absorption of CSF through arachnoid granulations. CSF pressure greater than 20 cm H20 is considered pathological of hydrocephalus, although CSF pressure in some forms of the disease can be lower than 20 cm H20. Venous blood pressure can range from about 4 cm H20 to about 11 cm H20 in non-hydrocephalic patients, and can be slightly elevated in diseased patients. While posture changes in patients, e.g., from supine to upright, affect CSF and venous pressures, the positive pressure gradient between ICP and venous pressure remains relatively constant. Momentary increases in venous pressure greater than CSF pressure, however, can temporarily disturb this gradient, for example, during episodes of coughing, straining, or valsalva.

Referring back to FIGS. 1A-1B, methods for deploying an endovascular CSF shunt 200 are described. A venous access point in the patient is created (e.g., via Seldinger technique to access the femoral vein) to facilitate navigation of catheters and guidewires to the caudal inferior vena cava. Catheters and guidewires are further navigated in a retrograde direction into the azygos vein 136 and into or proximate a venous branch 102 that extends adjacent or proximate to a nerve root 101. Venous branch 102 surrounds or lies adjacent dura layer 114 surrounding the nerve root 101 and the nerve root 101 extends through a spinal foramen and enters the CSF-filled LSAS 138. Next, the delivery catheter 300 is navigated from the venous access point, through the caudal vena cava and azygos vein, into venous branch 102. The delivery catheter 300 including the penetrating element 350 on the distal portion of the catheter can be advanced through the wall of venous branch 102, through dura layer 114 until the distal portion 344 of the catheter is disposed within the LSAS. The distal portion 202 of shunt 200 can be deployed from the opening 346 in the distal portion 344 of the catheter 300 such that the one or more CSF intake openings in the shunt 200 are disposed with LSAS 138, as shown in portion CC of FIGS. 1A-1B.

Alternate embodiments of the delivery catheter 300 are configured to receive a needle 352 in the delivery catheter lumen 305. When the distal portion 344 of the delivery catheter 300 is navigated to a target penetration site in the venous branch 102, the needle 352 can be advanced from the distal opening 346 of the catheter 300 to penetrate through the dura layer 114 into the LSAS 138. Portion BB of FIGS. 1A-1B shows the needle 352 advanced from the delivery catheter 300 through the dura layer 114, into the CSF filled LSAS 138. The delivery catheter 300 can include an expandable stent 304 (e.g., self-expanding) on the distal portion 344 of the catheter, as shown in portion BB of FIG. 1B. As the delivery catheter 300 is advanced from a guiding catheter, the stent 304 expands in venous branch 102 to secure the delivery catheter in place; this facilitates navigation of needle 352 from the delivery catheter opening 346 to access the LSAS 138 from the target penetration location in venous branch 102.

FIG. 2 depicts the deployment method and the shunt 200 shown in FIGS. 1A-1B, except that the deployment procedure and shunt 200 have been deployed in the thoracic SAS 800. Shunt deployments in the thoracic SAS 800 can be more challenging to the clinician and potentially riskier for patients based on the presence of the spinal cord 100 in the SAS and the proximity to a penetrating element during the procedure. The thoracic SAS 800 is unlike the lumber SAS where the base of the spinal cord 100 ends more cranially relative to the LSAS 138 locations, where the distal portion 202 of shunt 200 has been deployed as shown in FIGS. 1A-1B.

Venous branches 102 extending alongside or proximate the spinal SAS to the azygos or other veins present more challenging anatomy for deployment of an endovascular CSF shunt 200 than the intracranial venous sinuses. Unlike the venous sinuses secured to bony features in the skull, the venous branches 102 are unsupported veins that can move when advancing delivery catheter 300 and/or shunt 200 through the vessel; thus, venous branches 102 do not provide the same stable or secure platform free from movement provided by intracranial venous sinuses. In addition, venous branches 102 have a relatively flat cross-sectional profile compared to a more circular cross section observed in the inferior petrosal or sigmoid sinus. Venous branch lumens can also collapse and expand during normal cardiac cycles. Each of these features of venous branches 102 require greater emphasis on clinician skill and use of 3D imaging to facilitate deployment of CSF shunt 200 in the spinal SAS Procedural imaging is an important tools for all of the shunt deployment methods described herein. The clinician can obtain CT and/or MRI imaging (e.g., coronal, T2, thin cut MRI images with gadolinium contrast) studies of the patient's SAS and venous anatomy to ascertain the sizing and relative proximity between a target vessel (e.g., venous branch or internal cerebral vein) and SAS location to receive the distal portion 202 of shunt 200; such imaging can also be used to assess the volume of unobstructed CSF space relative to a target penetration site in a vessel where an anastomosis will be made during the shunt implant procedure. The clinician can use this pre-procedure imaging to select one or more preferred shunt deployment locations. Alternatively, a clinician can rely only on imaging acquired during the interventional procedure, for example, when deploying an endovascular shunt 200 in the LSAS 138. To the extent the clinician has created a 3D reconstruction of the patient's anatomy about a target penetration site (e.g., using 3D-rotational angiography or venography, intravascular ultrasound, or optical coherence tomography), the clinician can confirm the orientation and/or trajectory of the penetrating element 350 or needle 352 by combining the fluoroscopy and 3D reconstruction using a 3D road mapping technique. Optionally, the clinician can use the 3D reconstruction data to create a window representing the target penetration site; the 3D window and live fluoroscopy can be overlaid with respect to each other to provide further guidance for the clinician to a vessel wall or dura layer 114 at target penetration site. In addition, a 3D reconstruction of the anatomy of interest can be acquired and overlaid with pre-procedure CT or MRI data and/or live fluoroscopy during the shunt deployment procedure to facilitate delivery catheter navigation and shunt deployment.

Figure 4C:
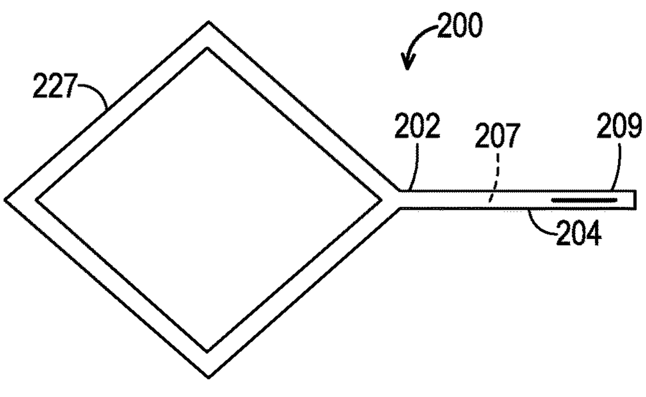

FIGS. 4A-4C depict embodiments of shunt 200. FIG. 4A shows the shunt 200 in a compressed delivery configuration; specifically, the distal anchor or anchoring mechanism 227 is collapsed or compressed to facilitate advancement through a delivery catheter when tracking to a target deployment site. A shunt penetrating element 250 is coupled to or disposed on the distal end of the anchoring mechanism 227, as shown in FIGS. 4A-4B. The FIG. 4C embodiment does not include a shunt penetrating element 250 is coupled to or disposed on the distal end of the anchoring mechanism 227. Referring to FIGS. 4A-4B, when the anchoring mechanism 227 is compressed within the lumen of a delivery catheter, the anchoring mechanism provides column strength support for the shunt 200 when advanced through dura layer 114 to access the CSF-filled LSAS. The shunt 200 can be advanced from the delivery catheter using a pusher tool to penetrate tissue(s) such that the distal portion 202 of the shunt 200 is disposed within a targeted CSF space (e.g., LSAS 138 or third ventricle 135). When the anchoring mechanism 227 advances out of the delivery catheter 300 and expands to a deployed configuration, as shown in FIGS. 4B-4C, the anchoring mechanism 227 secures the distal portion 202 of the shunt 200 in the CSF space. In the embodiment of FIG. 4B, the expansion of the anchoring mechanism 227 also shifts laterally or recesses of the shunt penetrating element 250 inside the outer perimeter of the expanded anchoring mechanism 227 to minimize the potential risks of trauma from leaving the shunt penetrating element 250 in the CSF space.

Figure 5:
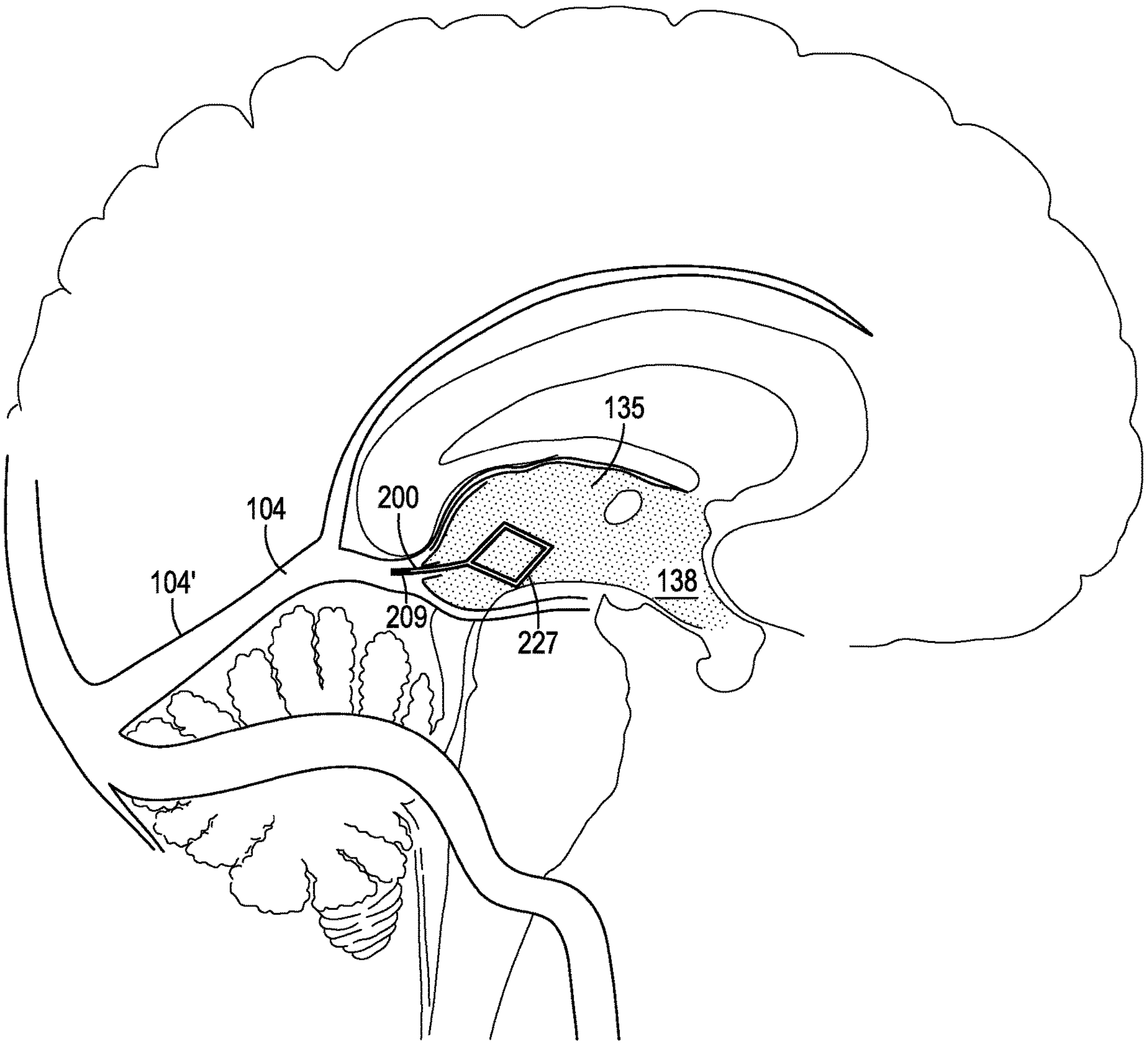
FIG. 5 is a sagittal view of the human brain and depicts an endovascular CSF shunt device according to embodiments of the disclosed inventions.

In some embodiments, the shunt 200 can be deployed in the third ventricle 135 to drain CSF from the SAS to a venous vessel, for example, for the treatment of obstructive hydrocephalus. FIG. 3 shows an intracranial venous pathway extending from a straight sinus distally to a vein of Galen and further distally into the internal cerebral vein 104. The straight sinus can be accessed by advancing a catheter and/or guidewire distally through the internal jugular vein, sigmoid sinus, and transverse sinus. Internal cerebral vein 104 extends alongside the CSF-filled third ventricle 135, as shown in FIG. 3. The wall of internal cerebral vein 104 comprises venous endothelium. Endovascular CSF shunt deployment methods can be performed to penetrate the venous endothelium separating the CSF-filled third ventricle 135 from the internal cerebral vein 104 and deploy the distal portion of embodiments of the shunt 200 in the third ventricle 135. Thus, delivery catheter 300 can be navigated through the straight sinus and vein of Galen to the internal cerebral vein 104. As described in connection with FIGS. 1A-1B, the penetrating element 350 disposed in the distal portion 344 of the delivery catheter, the needle 352 disposed within the delivery catheter (e.g., lumen 305) or the shunt penetrating element 250 can be used to access the CSF space in the third ventricle 135 from within internal cerebral vein 104. Following deployment, CSF flows into one or more CSF intake openings in the distal portion of shunt 200, through the lumen 207 of the shunt (FIGS. 4A-C), and out one or more CSF outflow openings in the proximal portion 204 of shunt 200 (e.g., through one way valve 209, FIGS. 4A-C). Embodiments of shunt 200 can be configured to extend the length of shunt body 203 such that the proximal portion 204 of the shunt and the one or more CSF outflow openings are disposed in the vein of Galen, in an intracranial venous sinus, or at an extracranial location in the venous system. FIG. 5 shows another embodiment of the shunt 200 draining CSF from the third ventricle 135 into the venous system.

The internal cerebral vein 104 presents more challenging anatomy for deployment of an endovascular CSF shunt device than the venous branches 102 disclosed herein or the intracranial venous sinuses. Unlike certain venous sinuses (e.g., inferior petrosal sinus) or venous branches 102, the internal cerebral vein 104 cannot be sacrificed or occluded during or after the endovascular shunt deployment procedure; injury or occlusion of this critical venous structure can cause ischemic stroke due to the critical drainage role played by the internal cerebral vein 104. The walls 104' of the internal cerebral vein 104 comprise thin endothelium (FIG. 5), unlike the relatively thicker dura layer 114 that separates the SAS from the intracranial venous sinuses or venous branches 102 (FIGS. 1A-16). Special care must be taken to avoid tearing this endothelium when accessing the third ventricle 135. Unlike the venous sinuses secured to bony features in the skull, the internal cerebral vein 104 is an unsupported vessel that can move when advancing the delivery catheter 300 and/or the shunt 200 through the vessel; thus, the internal cerebral vein 104 does not provide the same stable platform free from movement provided by intracranial venous sinuses. Each of these features of the internal cerebral veins 104 requires greater emphasis on clinician skill and use of 3D imaging methods disclosed herein to facilitate deployment of CSF shunt 200 in the third ventricle 135.

Figure 6A:
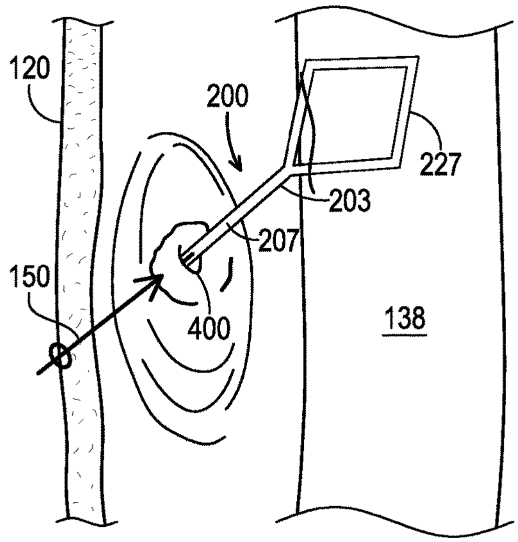
FIGS. 6A and 6B are schematic diagrams of a lumbar subarachonoid space of a human patient and depict endovascular CSF shunt devices according to embodiments of the disclosed inventions.
Figure 6B:
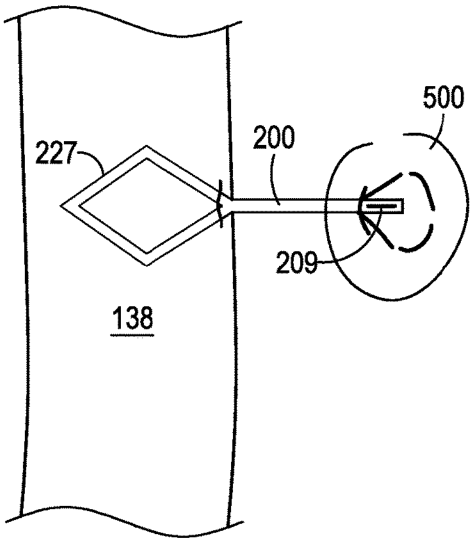

FIGS. 6A-6B depict embodiments of the shunt 200 draining CSF from a spinal SAS (e.g., lumbar or thoracic SAS 800) to an extra vascular location. The shunt 200 can be deployed percutaneously through skin 120 via a needle 150 advanced into the spinal SAS, as shown in FIG. 6A. Alternatively, some embodiments of the shunt 200 including the shunt penetrating element 250, the shunt 200 can be advanced percutaneously into the spinal SAS. In FIG. 6A, the distal anchoring mechanism 227 of the shunt 200 is deployed within the spinal SAS. The shunt 200 includes aA shunt body 203 that extends from the anchoring mechanism 227, through the dura lining the spinal SAS into a subcutaneous location. The shunt 200 of FIG. 6A includes a CSF dispersal mechanism 400 in fluid communication with shunt lumen 207 and one or more CSF intake openings in the distal portion of the shunt. The CSF dispersal mechanism 400 can comprise a sponge, multiple fluidic channels, or other structures intended to disperse CSF draining from shunt 200 into multiple extravascular locations.

FIG. 6B shows another embodiment of the shunt 200 draining CSF from the spinal SAS to an extravascular location. In FIG. 6B, the shunt 200 drains CSF out of valve 209 into a subcutaneous pocket 500. The pocket can be created surgically or with an angioplasty balloon and provides an extravascular drainage location for CSF removed from the spinal SAS where it is observed and dispersed into subcutaneous tissue.

Figure 7:
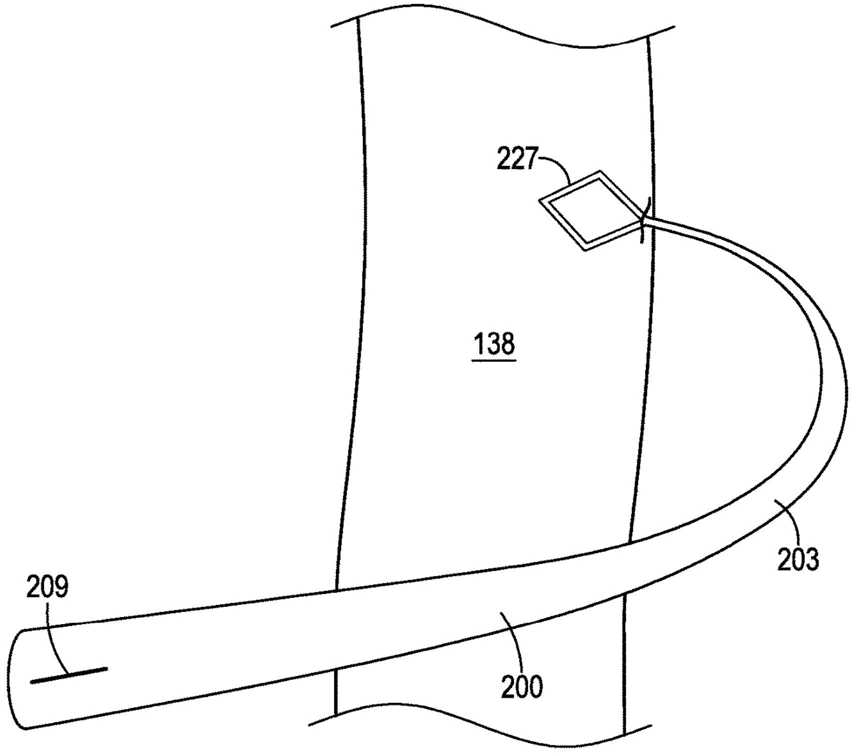
FIG. 7 is a schematic diagram of a lumbar subarachonoid space of a human patient and depicts an endovascular CSF shunt device according to embodiments of the disclosed inventions.

FIG. 7 shows another embodiment of the shunt 200 draining CSF from the spinal SAS to an extravascular location. Shunt 200 has an elongate shunt body 203 and the CSF lumen 207 that can be tunneled percutaneously to the peritoneal cavity. The peritoneal cavity represents another extravascular drainage location for CSF removed from the spinal SAS to drain and disperse within the body.

Figure 8:
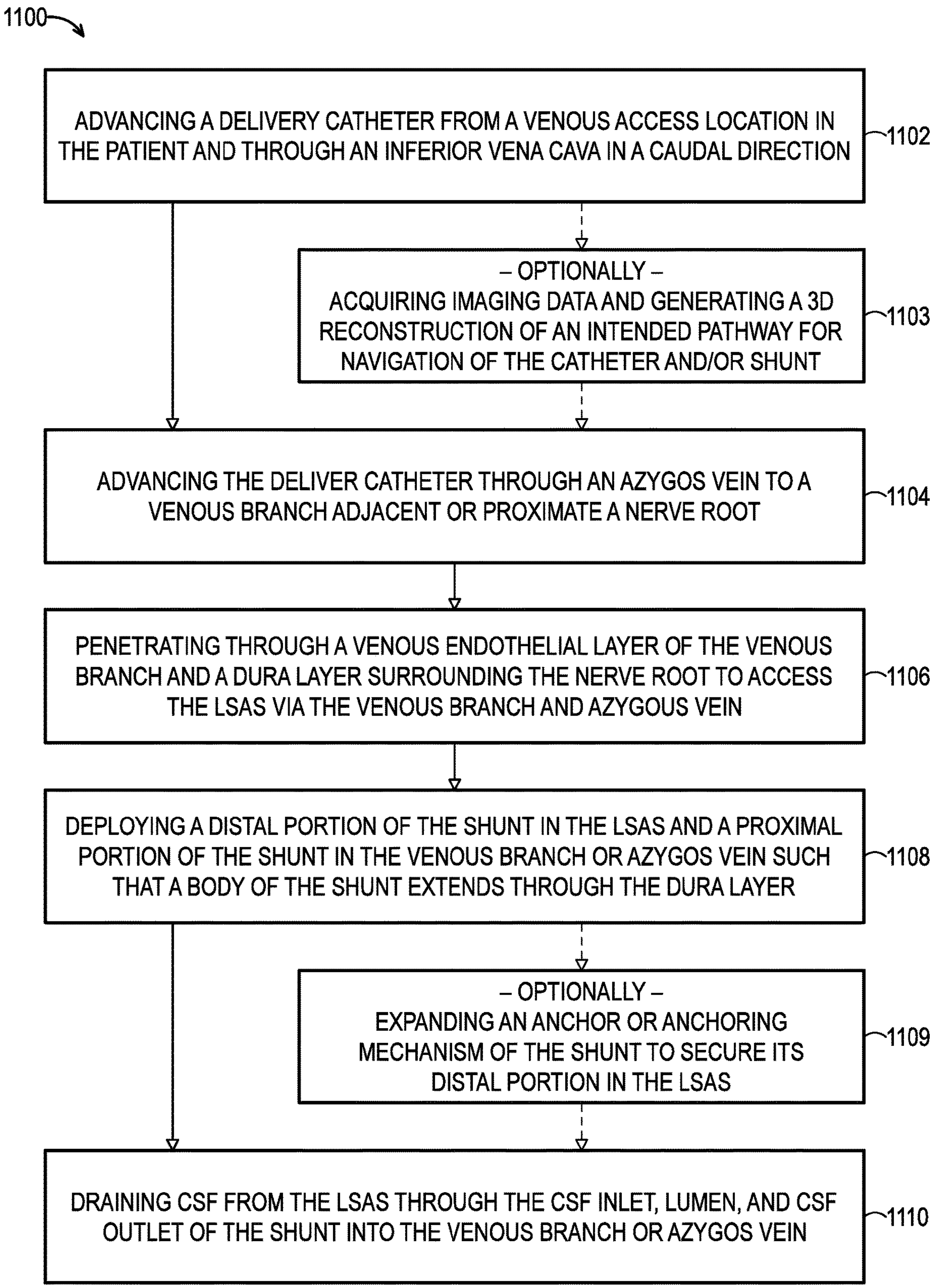
FIG. 8 is a flowchart of an exemplary method 1100 for draining CSF from a patient's LSAS into a venous system.

FIG. 8 is a flowchart summarizing an exemplary method 1100 for draining CSF from a patient's LSAS into a venous system. As shown in 1102, a surgeon, clinician or their like, advances a delivery catheter from a venous access location in the patient and through an inferior vena cava in a caudal direction. The delivery catheter may be any suitable delivery catheter configured to navigate through the vasculature into the LSAS of a patient. For example, the catheter used in the disclosed method is the delivery catheter 300 having the distal portion 344 with opening 346, the catheter defines the lumen 305 where the endovascular CSF shunt 200 is navigated through and delivered out of the opening 346 (FIG. 1B). In 1104, the surgeon, clinician or their like, further advances the deliver catheter through an azygos vein 136 to a venous branch adjacent or proximate a nerve root, the nerve root extending through a spinal foramen into the LSAS. The delivery catheter penetrates through a venous endothelial layer of the venous branch and a dura layer surrounding the nerve root to access the LSAS via the venous branch and azygous vein, in 1106. In 1108, the distal portion 202 of the shunt 200 is deployed in the LSAS and the proximal portion 204 of the shunt 200 is deployed in the venous branch or azygos vein, such that the body 203 of the shunt 200 extends through the dura layer 114. The shunt 200 having at least one CSF inlet in the distal portion 202, the lumen 207, and at least one CSF outlet in the proximal portion 204, where the shunt CSF inlet, lumen, and CSF outlet are in fluid communication therebetween. In 1110, CSF is drained from the LSAS through the CSF inlet, lumen, and CSF outlet of the shunt 200 into the venous branch or azygos vein.

According to the disclosed inventions, the method, sequence in said method, the shunt, and the delivery catheter configured to performed the draining of CSF from a patient's LSAS into a venous system described in FIG. 8 can be modified in a variety of ways. In some embodiments, 1106 can be accomplished by using the delivery catheter 300 having the penetrating element 350 disposed on or coupled to the distal portion 344 of the catheter (FIG. 1B). As such, penetrating the endothelial and dura layers, to access the LSAS from the venous branch and azygous vein comprises advancing the delivery catheter 300 and penetrating element 350 through the endothelium and dura such that the opening 346 of the delivery catheter is disposed within the spinal SAS. Optionally, in 1106, penetrating the endothelial and dura layers can be accomplished by using the shunt 200, when the shunt includes the penetrating element 250 disposed on or coupled to the distal portion 202 of the shunt (FIG. 1B). As a result, penetrating the endothelial and dura layers to access the LSAS from the venous branch and azygous vein comprises advancing the shunt 200 and penetrating element 250 through the dura layer 114, such that the CSF inlet of the shunt is disposed within the LSAS.

In some embodiments, optional in 1109, expanding an anchor or the anchoring mechanism 227 of the shunt 200 to secure the distal portion 202 of the shunt in the LSAS may be taken. Additionally, in 1109 securing the distal portion 202 may include recessing the penetrating element 250 of the shunt 200 inside an outer perimeter of the anchoring mechanism 227.

In some embodiments, the delivery catheter 300 configured to deliver the shunt 200 to drain CSF from a patient's LSAS into a venous system, comprises the stent 304 disposed around the distal portion 344 of the catheter (FIG. 1B). In said embodiment, the method further comprises expanding the stent 304 in the venous branch or azygos vein 136 to secure the distal portion 344 of the catheter 300 in the vessel.

In further embodiments, in 1108, penetrating the endothelial and dura layers can be accomplished by advancing the needle 352 through the delivery catheter lumen 305 out of the opening 346 of the catheter and further advancing the needle 352 through the dura layer 114 into the LSAS. In said embodiment, the needle 352 comprises a needle lumen and an opening in a distal portion of the needle lumen, and the shunt 200 can be disposed within the needle lumen. As such, deploying the distal portion 202 of the shunt in the LSAS comprises advancing the shunt 200 distally through the needle lumen and needle opening into the LSAS.

Optionally, the method for draining CSF from a patient's LSAS into a venous system may include of acquiring imaging data and generating a 3D reconstruction of an intended pathway from the venous branch or azygos vein 136 through the dura layer 114 to the LSAS, and using the 3D reconstruction to facilitate navigation of the delivery catheter or shunt from the venous branch into the LSAS (1103). The imaging data may include ultrasound or optical coherence tomography.

Additionally, the method 1100 for draining CSF from a patient's LSAS into a venous system, further comprises navigating an endovascular retrieval device through a patient's vasculature until the retrieval device is located at or proximate to the proximal portion 204 of the shunt 200; grasping or capturing the proximal portion 204 of the shunt 200 with the retrieval device; and removing the shunt 200 from the LSAS and the patient with the retrieval device.

Figure 9:
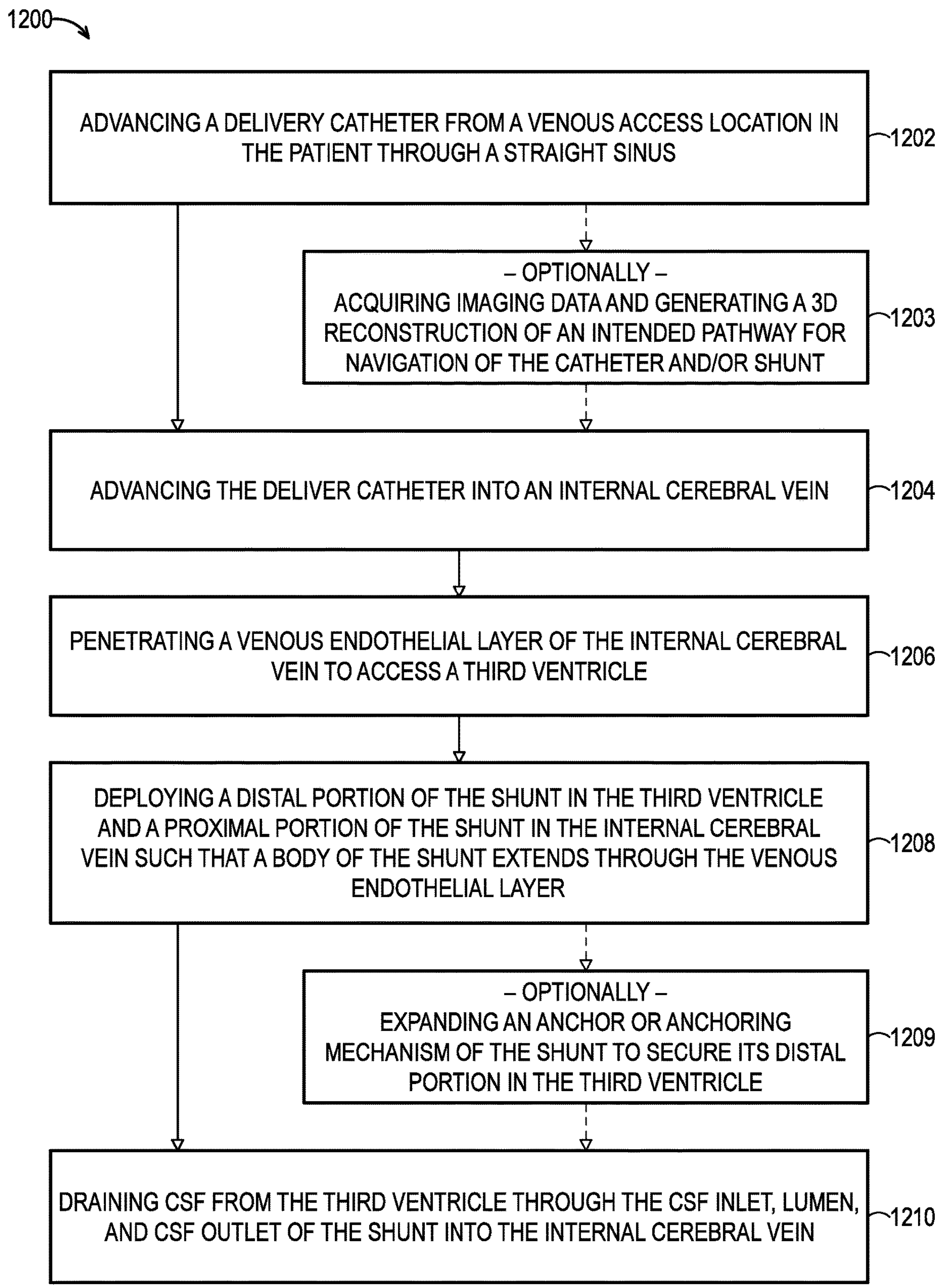
FIG. 9 is a flowchart of an exemplary method for draining CSF from a patient's subarachnoid space (SAS) to a venous system.

FIG. 9 is a flowchart summarizing an exemplary method 1200 for draining CSF from a patient's subarachnoid space (SAS) to a venous system. As shown in 1202, a surgeon, clinician or their like, advances a delivery catheter from a venous access location in the patient through a straight sinus. The delivery catheter may be any suitable delivery catheter configured to navigate through the vasculature into SAS. For example, the catheter used in the disclosed method is the delivery catheter 300 having the distal portion 344 with opening 346, the catheter defines the lumen 305 where the endovascular CSF shunt 200 is navigated through and delivered out of the opening 346 (FIG. 1B). In 1204, the surgeon, clinician or their like, further advances the deliver catheter 300 into an internal cerebral vein. The delivery catheter 300 penetrates a venous endothelial layer of the internal cerebral vein to access a third ventricle 135, in 1206. In 1208, the distal portion 202 of the shunt 200 is deployed in the third ventricle 135 and the proximal portion 204 of the shunt 200 is deployed in the internal cerebral vein such that the body 203 of the shunt extends through the venous endothelial layer. The shunt 200 having at least one CSF inlet in the distal portion 202, the lumen 207, and at least one CSF outlet in the proximal portion 204, where the shunt CSF inlet, lumen, and CSF outlet are in fluid communication therebetween. In 1210, CSF is drained from the third ventricle through the CSF inlet, lumen, and CSF outlet of the shunt into the internal cerebral vein.

According to the disclosed inventions, the method, sequence in said method, the shunt, and the delivery catheter configured to performed the draining of CSF from a patient's SAS into a venous system described in FIG. 9 can be modified in a variety of ways. In some embodiments, in 1208 the draining of CSF from a patient's SAS can be accomplished by using the delivery catheter 300 having the penetrating element 350 disposed on or coupled to the distal portion 344 of the catheter (FIG. 1B). As such, penetrating the venous endothelial layer comprises advancing the delivery catheter 300 and penetrating element 350 through venous endothelium, such that the opening 346 of the delivery catheter is disposed within the third ventricle 135 (FIGS. 3 and 5).

Optionally, in 1206 the method can be accomplished by using the shunt 200, when the shunt includes the penetrating element 250 disposed on or coupled to the distal portion 202 of the shunt (FIG. 1B). As a result, penetrating the venous endothelial layer to access the third ventricle 135 from the internal cerebral vein comprises advancing the shunt 200 and penetrating element 250 through the venous endothelium, such that the penetrating element 250 and CSF inlet of the shunt 200 are disposed within the third ventricle 135.

In some embodiments, the optionin 1209 of expanding an anchor or the anchoring mechanism 227 of the shunt 200 to secure the distal portion 202 of the shunt in the third ventricle 135 may be taken. Additionally, 1209 may include recessing the penetrating element 250 of the shunt 200 inside an outer perimeter of the anchoring mechanism 227. Additionally, in 1209, the method may include recessing the penetrating element 250 of the shunt 200 inside an outer perimeter of the anchoring mechanism 227.

In some embodiments, the delivery catheter 300 configured to deliver the shunt 200 to drain CSF from a patient's SAS into a venous system, comprises the stent 304 disposed around the distal portion 344 of the catheter (FIG. 1B). In said embodiment, the method further comprises expanding the stent 304 in the internal cerebral vein to secure the distal portion 344 of the catheter 300 in the vein.

In further embodiments, in 1206 the method can be accomplished by advancing the needle 352 through the delivery catheter lumen 305 out of the opening 346 of the catheter and further advancing the needle 352 through the venous endothelium into the third ventricle 135. In said embodiment, the needle 352 comprises a needle lumen and an opening in a distal portion of the needle lumen, and the shunt 200 can be disposed within the needle lumen. As such, deploying the distal portion 202 of the shunt in the third ventricle 135 comprises advancing the shunt 200 distally through the needle lumen and needle opening into the ventricle.

Optionally in 1203, the method for draining CSF from a patient's SAS into a venous system may include acquiring imaging data and generating a 3D reconstruction of an intended pathway from the internal cerebral vein through the venous endothelium into the third ventricle 135, and using the 3D reconstruction to facilitate navigation of the delivery catheter 300 and/or shunt 200 from the internal cerebral vein into the third ventricle 135. The imaging data may include ultrasound or optical coherence tomography.

In some embodiments of the method 1200, the body 203 of the shunt 200 extends into the internal cerebral vein and the proximal portion 204 of the shunt 200 further extends into the vein of Galen. Additionally, the proximal portion 204 of the shunt 200 may further extends into the strait sinus. Optionally, the proximal portion 204 of the shunt 200 may further extend to an extracranial venous location in the patient.

Figure 10:
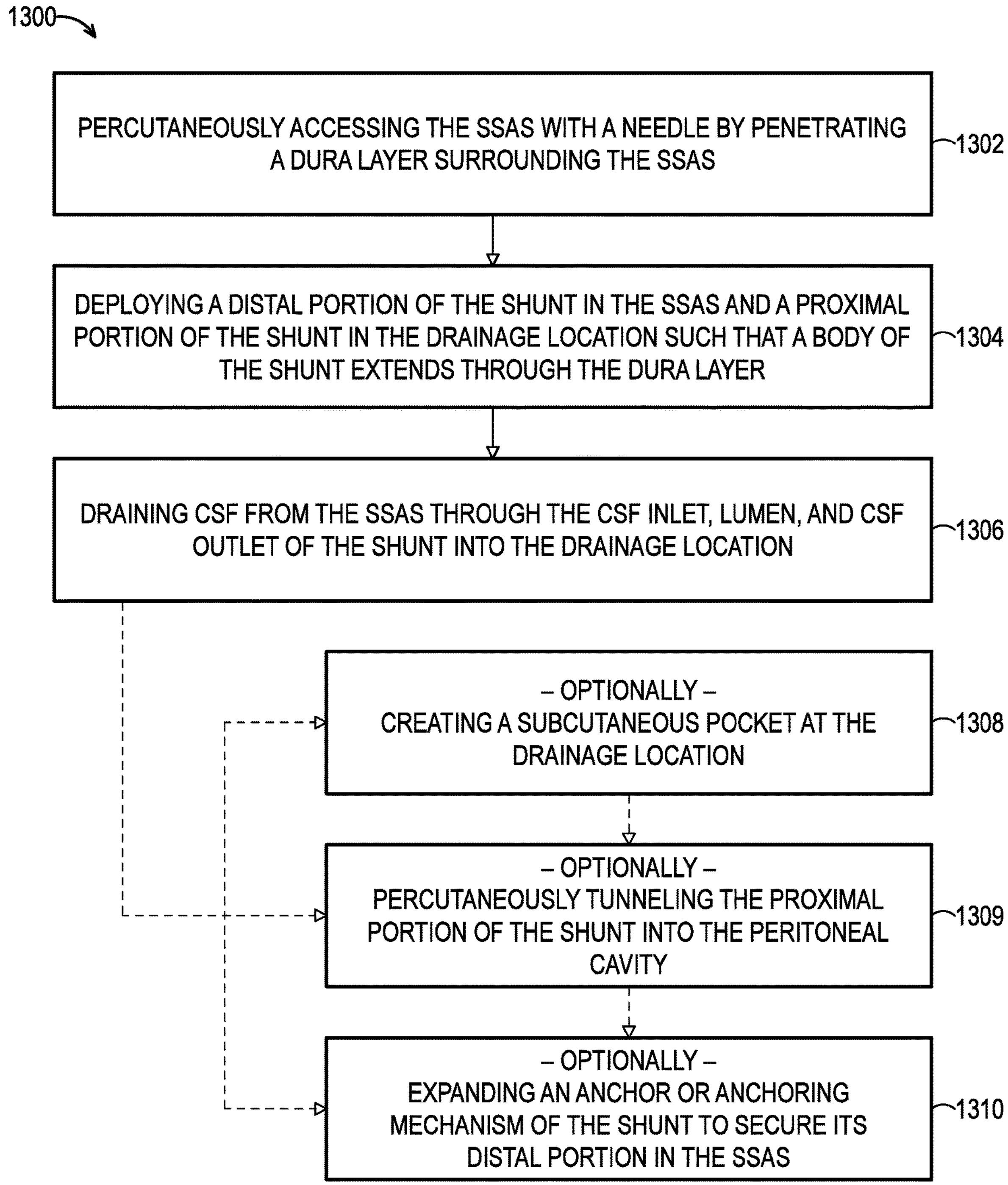
FIG. 10 is a flowchart of an exemplary method for draining CSF from a patient's spinal subarachnoid space (SSAS) to a subcutaneous drainage location.

FIG. 10 is a flowchart summarizing an exemplary method 1300 for draining CSF from a patient's spinal subarachnoid space (SSAS) to a subcutaneous drainage location. As shown in 1302, a surgeon, clinician or their like, may percutaneously access the SSAS with a needle by penetrating a dura layer surrounding the SSAS. In said embodiment, the needle comprises a needle lumen and an opening in a distal portion of the needle lumen, and an endovascular shunt device disposed within the lumen. In 1304, the distal portion 202 of the shunt 200 is deployed in the SSAS and the proximal portion 204 of the shunt 200 is deployed in the drainage location such that the body 203 of the shunt 200 extends through the dura layer. The shunt 200 having at least one CSF inlet in the distal portion 202, the lumen 207, and at least one CSF outlet in the proximal portion 204, where the shunt CSF inlet, lumen, and CSF outlet are in fluid communication therebetween. In 1306, CSF is drained from the SSAS through the CSF inlet, lumen, and CSF outlet of the shunt 200 into the drainage location. The shunt CSF outlet comprises a plurality of fluid passages to disperse CSF around the drainage location. In optional in 1308, the method 1300 further comprises creating a subcutaneous pocket at the drainage location. The drainage location comprises a peritoneal cavity of the patient. In option 1309, the method 1300 further comprises percutaneously tunneling the proximal portion of the shunt into the peritoneal cavity.

In the embodiments of method 1300, the shunt 200 comprises an anchor or the anchoring mechanism 227 disposed on or coupled to the distal portion 202 of the shunt 200 and wherein deploying the distal portion 202 of the shunt 200 in the SSAS further comprises expanding the anchor or the anchoring mechanism 227 to secure the distal shunt portion in the SSAS (in 1304).

Optionally, the shunt 200 may be deployed primarily in a horizontal plane in the patient to minimize over drainage of CSF in any of the methods 1100, 1200 and/or 1300.

In some embodiments where the shunt 200 is deployed temporarily in the patient following a subarachnoid hemorrhage, such method further comprises draining CSF and blood from the SAS into the venous system or extravascular location.

It should be appreciated that the inventions disclosed in FIGS. 1A-9 may include any methods and features disclosed herein, including methods and features disclosed in connection with different embodiments and the embodiments disclosed in the above-identified U.S. applications incorporated by references herein, in any combination as appropriate.

Any of the foregoing endovascular CSF shunt embodiments and deployment methods can be used to deploy a shunt temporarily instead of using an external ventricular drain (EVD) for the management of acute hydrocephalus following a ruptured cerebral aneurysm. For example, any of the shunts shown in FIGS. 1A-7 can be deployed following a subarachnoid hemorrhage, to facilitate CSF pressure management and drain blood and CSF from the SAS to another location in the body. In particular, deploying shunt 200 in the LSAS 138 or other spinal subarachnoid space away from the anatomic location of the ruptured aneurysm can mitigate against shunt occlusion from blood cells known to occlude EVDs. The distal anchoring mechanism 227 is collapsible such that application of a pull force to shunt 200 away from the SAS causes the anchoring mechanism to collapse for device withdrawal through dura layer 114 from the CSF space and its deployed location. Endovascular retrieval devices can be navigated through the venous system and used to grasp or capture the proximal and/or body portion of shunt 200 and remove the device from its deployed location in the patient. The ability of the anchoring mechanism 227 to collapse into a compressed delivery configuration during withdrawal from the shunt deployment location facilitates temporary use of the shunt 200 embodiments for the management of acute hydrocephalus.

The shunt deployment methods disclosed herein can deploy an endovascular CSF shunt in a horizontal or substantially horizontal plane in a patient when the patient is upright (e.g., as shown in FIGS. 1A-1B, 3, 6B, and 7). This deployment orientation advantageously minimizes or eliminates the risk of CSF over drainage when the patient changes posture (e.g., moving from supine to upright). VP shunt devices and certain endovascular shunt devices are typically deployed with the CSF inlet opening in a more cranial location in the patient compared to the CSF outlet location. During posture changes from supine to upright, a hydrostatic pressure gradient can form within the CSF lumen of these devices and cause problematic over drainage. The deployment methods disclosed herein, however, can overcome these limitations by deploying the endovascular shunt in a horizontal or substantially horizontal plane in a patient, thereby minimizing or eliminating the hydrostatic pressure gradient between the CSF inflow and outlet locations of the device. Further, embodiments of shunt 200 can be configured to have a relatively shorter overall length (e.g., less than 5 cm, 10 cm, 15 cm long, etc.) compared to conventional VP shunt devices to minimize risks of over-drainage from siphoning when a patient is in a supine position.

Although particular embodiments have been shown and described herein, it will be understood by those skilled in the art that they are not intended to limit the present inventions, and it will be obvious to those skilled in the art that various changes, permutations, and modifications may be made (e.g., the dimensions of various parts, combinations of parts) without departing from the scope of the disclosed inventions, which is to be defined only by the following claims and their equivalents. The specification and drawings are, accordingly, to be regarded in an illustrative rather than restrictive sense. The various embodiments shown and described herein are intended to cover alternatives, modifications, and equivalents of the disclosed inventions, which may be included within the scope of the appended claims.

What is claimed:

1. A method for draining cerebrospinal fluid (CSF) from a patient's lumbar subarachnoid space (LSAS) to a venous system, the method comprising:

advancing a delivery catheter from a venous access location in the patient and through an inferior vena cava in a caudal direction, the delivery catheter comprising a lumen with an opening on a distal portion of the catheter and an endovascular CSF shunt disposed within the lumen;

further advancing the deliver catheter through an azygos vein to a venous branch adjacent or proximate a nerve root, the nerve root extending through a spinal foramen into the LSAS;

penetrating through a venous endothelial layer of the venous branch and a dura layer surrounding the nerve root to access the LSAS via the venous branch and azygous vein;

deploying a distal portion of the shunt in the LSAS and a proximal portion of the shunt in the venous branch or azygos vein such that a body of the shunt extends through the dura layer, the shunt comprising at least one CSF inlet in the distal portion, a fluid lumen, and a CSF outlet in the proximal portion, the shunt CSF inlet, lumen, and CSF outlet in fluid communication; and draining CSF from the LSAS through the CSF inlet, lumen, and CSF outlet of the shunt into the venous branch or azygos vein.

2. The method of claim 1, the delivery catheter further comprising a penetrating element disposed on or coupled to the distal portion of the catheter, wherein penetrating the endothelial layer and dura layer to access the LSAS from the venous branch and azygous vein comprises advancing the delivery catheter and penetrating element through the endothelium and dura such that the open of the delivery catheter is disposed within the spinal SAS.

3. The method of claim 1, the shunt further comprising a penetrating element disposed on or coupled to the distal portion of the shunt, wherein penetrating the endothelial and dura layers to access the LSAS from the venous branch and azygous vein comprises advancing the shunt and penetrating element through the dura, such that the CSF inlet of the shunt is disposed within the LSAS.

4. The method of claim 3, wherein the shunt comprises an expandable anchor disposed on or coupled to the distal portion of the shunt and wherein deploying the distal portion of the shunt in the LSAS further comprises expanding the anchor to secure the distal shunt portion in the LSAS.

5. The method of claim 4, wherein expanding the anchor further comprises recessing the penetrating element inside an outer perimeter of the expanded anchor.

6. The method of claim 1, wherein the delivery catheter further comprises a stent disposed around the distal portion of the catheter, the method further comprising expanding the stent in the venous branch or azygos vein to secure the distal portion of the catheter in the vessel.

7. The method of claim 6 wherein penetrating the endothelial and dura layers to access the LSAS from the venous branch and azygous vein comprises advancing a needle disposed within the delivery catheter lumen from the opening in the distal catheter portion and further advancing the needle through the dura layer into the LSAS.

8. The method of claim 7, wherein the needle comprises a needle lumen and an opening in a distal portion of the needle lumen, the shunt disposed within the needle lumen, wherein deploying the distal portion of the shunt in the LSAS comprises advancing the shunt distally through the needle lumen and needle opening into the LSAS.

9. The method of claim 8 further comprising acquiring imaging data and generating a 3D reconstruction of an intended pathway from the venous branch or azygos vein through the dura layer to the LSAS; and using the 3D reconstruction to facilitate navigation of the delivery catheter or shunt from the venous branch into the LSAS.

10. The method of claim 9, wherein the imaging data comprises ultrasound or optical coherence tomography.

11. The method of claim 1, further comprising:

navigating an endovascular retrieval device through a patient's vasculature until the retrieval device is located at or proximate to the proximal portion of the shunt;

grasping or capturing the proximal portion of the shunt with the retrieval device; and removing the shunt from the LSAS and the patient with the retrieval device.

* * * * *